United States Patent
Gowani et al.

(10) Patent No.: US 10,434,119 B2
(45) Date of Patent: Oct. 8, 2019

(54) PHARYNGEAL OR BUCCAL CAVITY RINSE AND PROCESS OF USE THEREOF

(71) Applicants: Jehangir Gowani, Ann Arbor, MI (US); Ian Vonwald, Ann Arbor, MI (US); Xiaojiang Wang, Ann Arbor, MI (US); Evan Boyst, Ann Arbor, MI (US); Shri Thanedar, Ann Arbor, MI (US)

(72) Inventors: Jehangir Gowani, Ann Arbor, MI (US); Ian Vonwald, Ann Arbor, MI (US); Xiaojiang Wang, Ann Arbor, MI (US); Evan Boyst, Ann Arbor, MI (US); Shri Thanedar, Ann Arbor, MI (US)

(73) Assignee: Gargle Water, Inc., McKinney, TX (US)

( * ) Notice: Subject to any disclaimer, the term of this patent is extended or adjusted under 35 U.S.C. 154(b) by 0 days.

(21) Appl. No.: 15/405,745

(22) Filed: Jan. 13, 2017

(65) Prior Publication Data
US 2017/0196783 A1   Jul. 13, 2017

Related U.S. Application Data

(60) Provisional application No. 62/278,188, filed on Jan. 13, 2016.

(51) Int. Cl.
| | | |
|---|---|---|
| A61K 33/16 | (2006.01) | |
| A61K 33/40 | (2006.01) | |
| A61K 9/00 | (2006.01) | |
| A61K 33/20 | (2006.01) | |
| A61K 47/02 | (2006.01) | |
| A61K 31/198 | (2006.01) | |
| A61K 31/737 | (2006.01) | |

(52) U.S. Cl.
CPC .............. A61K 33/40 (2013.01); A61K 9/006 (2013.01); A61K 9/0043 (2013.01); A61K 9/0053 (2013.01); A61K 31/198 (2013.01); A61K 31/737 (2013.01); A61K 33/16 (2013.01); A61K 33/20 (2013.01); A61K 47/02 (2013.01)

(58) Field of Classification Search
CPC .................................................. A61K 33/40
See application file for complete search history.

(56) References Cited

U.S. PATENT DOCUMENTS

| | | | | |
|---|---|---|---|---|
| 4,947,620 A | * | 8/1990 | Carter | B65B 11/52 53/425 |
| 5,104,644 A | * | 4/1992 | Douglas | A61K 8/22 424/49 |
| 5,392,947 A | | 2/1995 | Gentile | |
| 6,187,332 B1 | * | 2/2001 | Gern | A61K 9/0043 424/400 |
| 8,906,348 B2 | | 12/2014 | Narasimhan et al. | |
| 9,084,902 B2 | | 7/2015 | Mordas et al. | |
| 2004/0057907 A1 | * | 3/2004 | Mackles | A61K 9/0043 424/45 |
| 2005/0069503 A1 | * | 3/2005 | Larsen | A61C 19/063 424/53 |
| 2009/0123570 A1 | * | 5/2009 | Warner | A61K 33/14 424/677 |
| 2011/0059919 A1 | * | 3/2011 | Grassauer | A61K 31/737 514/54 |
| 2017/0196783 A1 | | 7/2017 | Gowani et al. | |

FOREIGN PATENT DOCUMENTS

| | | |
|---|---|---|
| KR | 1020130123861 A | 11/2013 |
| WO | 2010054083 A2 | 5/2010 |

OTHER PUBLICATIONS

Sluka et al (Muscle and Nerve, v24, 11, 2001, 37-46).*
Spijkervet, F.K.L. et al., "Colonisation index of the oral cavity: a novel technique for monitoring colonisation defence", Microbial Ecology in Health and Disease (1989), pp. 145-151, vol. 2, Copyright John Wiley & Sons, Ltd. (1989).
Millet, J. et al., "Antithrombotic and Anticoagulant Activities of a Low Molecular Weight Fucoidan by the Subcutaneous Route", Thromb Haemost (1999), pp. 391-395, vol. 81, Copyright Schattauer Verlag, Stuttgart (1999); http://www.thrombosis-online.com.

(Continued)

*Primary Examiner* — Benjamin J Packard
(74) *Attorney, Agent, or Firm* — Avery N. Goldstein; Blue Filament Law PLLC

(57) ABSTRACT

A storage stable package is provided that includes a polymeric bottle having a volume filled with an aqueous saline composition acidified with an acid to a pH of 2 to 9 and having a hypertonic saline concentration relative to saliva and blood, or an aqueous hydrogen peroxide composition acidified with an acid to a pH of 2.7 to 5.3 and having a hydrogen peroxide concentration 0.5 to 3 total weight percent, either to achieve a storage stability at 20 degrees Celsius of the composition of at least 10 weeks. The aqueous composition is independent of a synthetic antimicrobial. A cap is provided that is complementary a package opening for selectively sealing the aqueous saline composition within the volume. A process for treating an infection of a pharyngeal or buccal cavity is provided that includes rinsing with one of the aqueous saline composition. The aqueous saline composition is then expectorated.

23 Claims, No Drawings

(56) References Cited

OTHER PUBLICATIONS

Decker, E.M. et al., "A synergistic chlorhexidine/chitosan combination for improved antiplaque strategies", Journal of Periodontal Research (2005), pp. 373-377, vol. 40, Copyright Blackwell Munksgaard Ltd (2005); doi:10.1111/j.1600-0765.2005.00817.x.
Taylor, Peter W. et al., "Antimicrobial properties of green tea catechins", Food Science and Technology Bulletin (2005), pp. 71-81, vol. 2, Food Sci Technol Bull. Author manuscript; available in PMC Oct. 19, 2009.
Cushnie, T.P.T. and Lamb, Andrew J. "Antimicrobial activity of flavonoids", International Journal of Antimicrobial Agents (2005), pp. 343-356, vol. 26, Copyright Elsevier B.V. and the International Society of Chemotherapy (2005); doi:10.1016/j.ijantimicag.2005.09.002; http://www.ischemo.org.
Kulikov, S.N. et al., "Effect of the Molecular Weight of Chitosan on Its Antiviral Activity in Plants", Applied Biochemistry and Microbiology (2006), pp. 200-203, vol. 42, Issue 2, Copyright MAIK "Nauka/Interperiodica" (Russia) (2006); DOI: 10.1134/S0003683806020165.
Singh, Meenakshi et al., "Antimicrobial Flavonoid Rutin from Pteris Vittata L. Against Pathogenic Gastrointestinal Microflora", American Fern Journal (2008), pp. 98-103, vol. 98, Issue 2; http://www.bioone.org/doi/full/10.1640/0002-8444%282008%2998%5B98%3AAFRFPV%5D2.0.CO%3B2.
Li, Bo et al., "Fucoidan: Structure and Bioactivity", Molecules, Aug. 12, 2008, pp. 1671-1695, vol. 13, Copyright the authors; licensee Molecular Diversity Preservation International, Basel, Switzerland (2008); DOI: 10.3390/molecules13081671; www.mdpi.org/molecules.
Ushiyama, Mina et al., "Analysis of the stability and microbiological safety of aznol saline gargle in hospital preparations widely used for the treatment of oral cancer patients with oral mucositis", Dental Medicine Therapy (2008), pp. 143-150, vol. 27, Issue 3; https://doi.org/10.11263/jsotp1982.27.143.
Sensabaugh, Cynthia and Sagel, Mary Elizabeth, "Stannous Fluoride Dentifrice with Sodium Hexametaphosphate: Review of Laboratory, Clinical and Practice-Based Data", The Journal of Dental Hygiene (2009), pp. 1-9, vol. 83, Issue 2.
Goy, Rejane C. et al., "A Review of the Antimicrobial Activity of Chitosan", Polímeros: Ciência e Tecnologia (2009), pp. 241-247, vol. 19, Issue 3.
Kantachumpoo, Attachai and Chirapart, Anong, "Components and Antimicrobial Activity of Polysaccharides Extracted from Thai Brown Seaweeds", Kasetsart J. (Nat. Sci.) (2010), pp. 220-233, vol. 44, Issue 2.
Ryan, William R. and Hwang, Peter H., "Safety of a Preservative-Free Acidified Saline Nasal Spray", Arch Otolaryngol Head Neck Surg, Nov. 2010, pp. 1099-1103, vol. 136, Issue 11, Copyright American Medical Association (2010); http://www.archoto.com.
Bharate, Sonali S. et al., "Interactions and incompatibilities of pharmaceutical excipients with active pharmaceutical ingredients: a comprehensive review", J. Excipients and Food Chem. (2010), pp. 3-26, vol. 1, Issue 3, Copyright IPEC-Americas Inc (2010).
Jiao, Guangling et al., "Chemical Structures and Bioactivities of Sulfated Polysaccharides from Marine Algae", Marine Drugs, Feb. 8, 2011, pp. 196-223, vol. 9, Copyright the authors; licensee MDPI, Basel, Switzerland (2011); doi:10.3390/md9020196; www.mdpi.com/journal/marinedrugs.
Hendra, Rudi et al., "Flavonoid Analyses and Antimicrobial Activity of Various Parts of Phaleria macrocarpa (Scheff.) Boerl Fruit", International Journal of Molecular Sciences, May 27, 2011, pp. 3422-3431, vol. 12, Copyright the authors; licensee MDPI, Basel, Switzerland (2011); doi:10.3390/ijms12063422; www.mdpi.com/journal/ijms.
Ale, Marcel Tutor et al., "Important Determinants for Fucoidan Bioactivity: A Critical Review of Structure-Function Relations and Extraction Methods for Fucose-Containing Sulfated Polysaccharides from Brown Seaweeds", Marine Drugs, Oct. 24, 2011, pp. 2106-2130, vol. 9, Copyright the authors; licensee MDPI, Basel, Switzerland (2011); doi:10.3390/md9102106; www.mdpi.com/journal/marinedrugs.
Ai, Hui et al., "Antioxidant, antifungal and antiviral activities of chitosan from the larvae of housefly, Musca domestica L." Food Chemistry, Nov. 13, 2011, pp. 493-498, vol. 132, Copyright Elsevier Ltd. (2011); www.elsevier.com/locate/foodchem.
Siedenbiedel, Felix and Tiller, Joerg C., "Antimicrobial Polymers in Solution and on Surfaces: Overview and Functional Principles", Polymers, Jan. 9, 2012, pp. 46-71, vol. 4, Copyright the authors; licensee MDPI, Basel, Switzerland (2012); www.mdpi.com/journal/polymers.
Patel, Seema, "Therapeutic importance of sulfated polysaccharides from seaweeds: updating the recent findings", 3 Biotech, Apr. 15, 2012, pp. 171-185, vol. 2, Copyright the Author(s) (2012); DOI 10.1007/s13205-012-0061-9.
Chen, Chih-Yu and Chung, Ying-Chien, "Antibacterial effect of water-soluble chitosan on representative dental pathogens Streptococcus mutans and Lactobacilli brevis", J Appl Oral Sci. (2012), pp. 620-627, vol. 20, Issue 6; www.scielo.br/jaos.
Lee, Kyung-Yeol et al., "Synergistic effect of fucoidan with antibiotics against oral pathogenic bacteria", Archives of Oral Biology (2013), pp. 482-492, vol. 58, Copyright Elsevier Ltd. (2012); http://dx.doi.org/10.1016/j.archoralbio.2012.11.002; http://www.elsevier.com/locate/aob.
Marudhupandi, Thangapandi et al., "Antibacterial effect of fucoidan from Sargassum wightii against the chosen human bacterial pathogens", International Current Pharmaceutical Journal, Sep. 2013, pp. 156-158, vol. 2, Issue 10, Copyright Marudhupandi and Kumar; licensee Saki Publishing Club (2013); http://www.icpjonline.com/documents/Vol2Issue10/01.pdf.
Lee, Dong-Hun et al., "In Vitro Virucidal Effect of Mouthrinse Containing C31G on Seasonal Influenza Viruses", J. Microbiol. Biotechnol., Apr. 1, 2014, pp. 921-924, vol. 24, Issue 7, Copyright The Korean Society for Microbiology and Biotechnology (2014); http://dx.doi.org/10.4014/jmb.1312.12055.
Kalil, David M. et al., "Novel Preoperative Pharmacologic Methods of Preventing Postoperative Sore Throat due to Tracheal Intubation", AANA Journal, Jun. 2014, pp. 188-197, vol. 82, Issue 3; http://www.aana.com/aanajournalonline.
Choi, Sung-Mi et al., "Synergistic Effect between Fucoidan and Antibiotics against Clinic Methicillin-Resistant Staphylococcus aureus", Advances in Bioscience and Biotechnology, Apr. 16, 2015, pp. 275-285, vol. 6, Copyright the authors and Scientific Research Publishing Inc. (2015); http://dx.doi.org/10.4236/abb.2015.64027;http://www.scirp.org/journal/abb/.
International Search Report dated Feb. 2, 2018 for International Application No. PCT/US2017/041365 filed Jul. 10, 2017.

\* cited by examiner

PHARYNGEAL OR BUCCAL CAVITY RINSE AND PROCESS OF USE THEREOF

RELATED APPLICATIONS

This application claims priority benefit of U.S. Provisional Application Ser. No. 62/278,188 filed 13 Apr. 2016; the contents of which are hereby incorporated by reference.

FIELD OF THE INVENTION

The present invention in general relates to a pharyngeal or buccal cavity rinse solution that is storage stable, and in particular to an acidified rinse that does not rely on sensitizing antimicrobials to achieve storage stability.

BACKGROUND OF THE INVENTION

The preparation of a hypertonic salt water solution for immediate use as a gargle and mouthwash is a well-known treatment and preventative for infections of the mouth and throat. Salt water will reduce swollen tissues and draw infection from any abscesses or infections present. Bacteria are single-celled organisms which can multiply rapidly under conditions found in the pharyngeal or buccal cavity. When the reproductive rate of certain strains of bacteria outstrips the immune response, soreness, inflammation, and even fever can result. While some bacteria are actually beneficial to the human body pathogenic bacteria are often directly responsible for many human illnesses, with one of the most common human illnesses being a sore throat.

Gargling with hypertonic salt water causes osmosis to occur. Osmosis is the process by which solvents, such as water, separated by a semi-permeable membrane, move from a region of lower concentration to higher concentration in order to equilibrate. By introducing hypertonic saline into the pharyngeal or buccal cavity, bacterial dehydration and lysis occurs.

Inflammation, regardless of the cause, is also reduced as water is drawn from tissues by osmosis. Hypertonic saline solution also helps to draw liquid from the throat. Edemas naturally occur during an infection, and by drawing it out of the tissue, swelling is reduced. This in turn reduces pain.

The salt may also kill some bacteria, but many strains are now resistant to mild levels of salt. It is a misconception to think that the salt water will directly kill off the bacteria. Gargling or rinsing with hypertonic saline solution simply creates a dehydrated environment that the bacteria find less hospitable and potentially dangerous and has implicated in reducing biofilm formation by *Pseudomonas aeruginosa* and the production of associated virulence factors. Hypertonic saline also appears to increase the levels of two thiols that are protective against oxidative injury namely, glutathione and thiocyanate.

Unfortunately, diluted hypertonic saline ready for use as a mouthwash or gargle is a growth medium for halophilic organisms that include algae, fungi, and bacteria. Exemplary organism include *Dunaliella Halobacteria, Halorhabdus*, and *Eurotiomycetes*. As a result, the production and storage of a hypertonic saline of a concentration suitable as a mouth wash or gargle is problematic. While such solutions can be pasteurized or radiation sterilized for single use applications, such techniques are both expensive and ineffective a multiple use container is contemplated. As an alternative, low molecular weight, synthetic organic molecules have been used as antimicrobials to afford storage stability. Unfortunately, a number of people have sensitivity to such antimicrobials, while still others find the flavor profile of antimicrobials unpleasant. Additionally, the usage of such antimicrobials has raised concerns about downstream effects on the environment and induction of resistance in target microbes.

Additionally, a certain class of individuals, including those with hypertension cannot safely use a saline rinse. As a result, for such individuals to treat the pharyngeal or buccal cavity for infections, hydrogen peroxide is often used. While 3% hydrogen peroxide in water has stability of greater than one year in a sealed container, opening such a bottle decreases the shelf life. Also, metal ions present in the solution, leached from a container, or introduced through contamination induce catalytic decomposition to water.

Thus, there exists a need for a mouth wash and gargle solutions that are prepared at ready to use concentrations that have storage stability without resort to small molecule synthetic antimicrobials.

SUMMARY OF THE INVENTION

A storage stable package is provided that includes a polymeric bottle having a volume filled with an aqueous saline composition acidified with an acid to a pH of 2 to 9 and having a hypertonic saline concentration relative to saliva and blood to achieve a storage stability at 20 degrees Celsius of the composition of at least 10 weeks. The aqueous composition is independent of a synthetic antimicrobial. A cap is provided that is complementary a package opening for selectively sealing the aqueous saline composition within the volume.

A storage stable package is provided that includes a polymeric bottle having a volume filled with an aqueous hydrogen peroxide composition acidified with an acid to a pH of 2.7 to 5.3 and having a hydrogen peroxide concentration 0.5 to 3 total weight percent of the aqueous hydrogen peroxide composition to achieve a storage stability at 20 degrees Celsius of the composition of at least 10 weeks. The aqueous composition is independent of a small molecule organic synthetic antimicrobial. A cap is provided that is complementary a package opening for selectively sealing the aqueous saline composition within the volume.

A process for treating an infection of a pharyngeal or buccal cavity is provided that includes rinsing the pharyngeal or buccal cavity with one of the aqueous saline composition of above for an amount of time sufficient to treat the infection. The aqueous saline composition is then expectorated.

DETAILED DESCRIPTION OF THE INVENTION

The present invention has utility as a pharyngeal or buccal cavity rinse in the forms of a gargle or mouthwash to treat infections of such regions. Without intending to be bound to a particular theory, an inventive rinse is hypertonic relative to saliva and blood. This hypertonicity is believed to not only desiccate pathogens, but also reduce inflammation through drawing of excess fluid from inflamed tissue. Acidification of the rinse provides storage stability without resort to small organic molecule synthetic antimicrobials.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

As used herein a "small organic molecule synthetic antimicrobial" defines a molecule that has a molecular weight of less than 1000 atomic mass units that is present for this purpose. Specific "small organic molecule synthetic antimicrobials" excluded from inventive compositions include benzalkonium chloride, cetylpyridinium chloride, chlorhexidine gluconate, methylparaben, methyl salicylcate, and domiphen bromide.

A storage stable package is provided includes a polymeric bottle with a cap for selectively enclosing a volume. An aqueous saline composition is provided that has been acidified with an acid to a pH of 2 to 9 and having a hypertonic saline concentration relative to saliva and blood. Alternatively, an aqueous hydrogen peroxide composition is provided that has been acidified with an acid to a pH of 2.7 to 5.3 and having a hydrogen peroxide concentration 0.5 to 3 total weight percent of the aqueous hydrogen peroxide. The saline or peroxide composition is placed in the bottle to achieve a storage stability at 20 degrees Celsius of the composition of at least 10 weeks. The saline or peroxide composition being independent of a synthetic antimicrobial.

A plastic bottle of an inventive package is formed from a variety of polymers suitable for acid aqueous solution packaging. These polymers illustratively include polyethylene, polypropylene, polyvinyl chloride, polyterephthalates, and block co-polymers containing any of the aforementioned as blocks therein. A cap sized and shaped to engage a plastic bottle opening is likewise formed of any of the aforementioned polymers. It is appreciated that bottle and cap are each independently formed as transparent, translucent, or opaque articles. In certain inventive embodiments, both the bottle and the cap are opaque.

An aqueous saline composition according to the present invention is formed by dissolution of sodium chloride in sterile water. In some inventive embodiments, the water has been deionized. The sodium chloride is present from 1.7 to 5.0 total weight percent of the solution. In certain inventive embodiments, the sodium chloride is present from 1.8 to 2.8 total weight percent. In some inventive embodiments, the saline composition pH is between 3.0 and 7.0. In still other, embodiments, the saline composition pH is between 3.6 and 5.4. Generally, an inventive composition is free of phenols and ethanol.

A hydrogen peroxide composition is provided that includes hydrogen peroxide present in a concentration 0.5 to 3 total weight percent. Such a solution is readily formed through the dilution of more concentrated hydrogen peroxide. Owing to the role spurious metal ions play in catalytic degradation of hydrogen peroxide, the use of deionized water is preferred. In some inventive embodiments, the saline composition pH is between 3.0 and 5.0. In still other, embodiments, the saline composition pH is between 3.6 and 4.4.

Acids suitable for pH reduction, or acidification, to form an inventive package of mouth wash or gargle include those that are compatible with human mucous membrane contact in diluted form and compatible with other composition and bottle components. Acids operative herein illustratively include hydrochloric, hydrobromic, lactic, citric, malic, acetic, benzoic, ascorbic, tartric, oxalic, tannic, butyric, caffeotannic, phosphoric, sulfuric, nitric, or a combination thereof.

An inventive composition, regardless of whether saline or hydrogen peroxide based, includes various adjuvants. Adjuvants operative herein in terms of function illustratively include antimicrobial, flavorants, desensitizer, a fluoridation agent, or a combination thereof.

An antimicrobial operative herein illustratively includes sodium benzoate, benzoic acid, methylparaben, ethylparaben, propylparaben, paraben derivatives, or a combination thereof. Typical quantities of an antimicrobial, if present, in the inventive composition range from 0.01-3 total weight percent.

A flavorant operative herein illustratively includes an essential oil, a water soluble plant extract, an alcohol soluble plant extract, or a combination thereof. Exemplary flavorants include cloves, culeb oil, cedarwood oil, eucalyptus oil, lemon oil, menta arvensis extracts (e.g. menthol), mint, wintergreen oil, peppermint oil, mint tea concentrate, sucralose, sodium saccharin, other artificial and natural fruit flavors, and combinations thereof. Typical quantities of an anti-oxidant, if present, in the inventive composition range from 0.01-3 total weight percent.

A desensitizer operative herein illustratively includes arginine, camphor, potassium nitrate, potassium chloride, potassium citrate, silver nitrate, zinc chloride, gluteraldehyde, strontium chloride hexahydrate, sodium fluoride, stannous fluoride, strontium chloride, potassium oxalate, calcium phosphate, nano-hydroxyapatite, or a combination thereof. Typical quantities of a desensitizer, if present, in the inventive composition range from 0.1-8 total weight percent.

A fluoridation agent operative herein illustratively includes sodium fluoride, calcium fluoride, hexafluorosilicate, or a combination thereof. Typical quantities of a fluoridation agent, if present, in the inventive composition range from 0.01-0.2 total weight percent.

In some inventive embodiments, fucoidan is present. Fucoidan is a sulfated polysaccharide. As used herein, fucoidan is intended to encompass both F-fucoidan, which is composed predominantly of sulfated esters of fucose, and U-fucoidan, which contains appreciable amounts of glucuronic acid (10-30 weight %). Typical quantities of fucoidan, if present, in the inventive composition range from 0.01-2.0 total weight percent.

It has been discovered to improve the function of saline or hydrogen peroxide composition according to the present invention in terms of treating or preventing infections of the pharyngeal or buccal cavities.

The present invention is further detailed with respect to the following nonlimiting examples. Unless otherwise specified, the percentages detailed herein are total weight percent of the inventive formulation.

EXAMPLE 1-6

A series of inventive compositions are developed with a saline solution base as detailed in Tables 1-4:

TABLE 1

Formulation of saline gargles with fucoidan.

| Saline Gargle with Fucoidan | Example 1 % (w/w) | Example 2 % (w/w) |
| --- | --- | --- |
| Water | 97.49 | 97.3 |
| NaCl | 2.25 | 2.25 |
| Fucoidan | 0.1 | 0.2 |
| HCl 10% | 0.08495 | 0.08 |
| Sodium Benzoate | 0.05 | 0.05 |
| Menthol | 0.025 | 0.05 |
| pH | 4.01 | 3.75 |
| Total osmolarity | 0.78 | 0.78 |

TABLE 2

Formulation of saline gargle without Fucoidan.

| Saline Gargle without Fucoidan | Example 3 |
|---|---|
| Water | 97.59 |
| NaCl | 2.25 |
| HCl 10% | 0.08495 |
| Sodium Benzoate | 0.05 |
| Menthol | 0.025 |
| pH | 3.72 |
| Total osmolarity | 0.78 |

TABLE 3

Formulation of saline mouthwash with fucoidan.

| Saline Mouth Wash with Fucoidan | Example 4 % (w/w) | Example 5 % (w/w) |
|---|---|---|
| Water | 97.185 | 97.085 |
| NaCl | 1.8 | 1.8 |
| Sodium Benzoate | 0.05 | 0.05 |
| Fucoidan | 0.1 | 0.2 |
| Arginine | 0.8 | 0.8 |
| Sodium Fluoride | 0.04 | 0.04 |
| Menthol | 0.025 | 0.025 |
| pH | 6.05 | 6.08 |
| Total osmolarity | 0.69 | 0.69 |

TABLE 4

Formulation of saline mouthwash without fucoidan.

| Saline Mouth Wash without Fucoidan | Example 6 % (w/w) |
|---|---|
| Water | 97.285 |
| NaCl | 1.8 |
| Sodium Benzoate | 0.05 |
| Arginine | 0.8 |
| Sodium Fluoride | 0.04 |
| Menthol | 0.025 |
| pH | 6.5 |
| Total osmolarity | 0.69 |

EXAMPLE 7-9

A series of inventive compositions are developed with a hydrogen peroxide solution base as detailed in Tables 5 and 6:

TABLE 5

Formulation of hydrogen peroxide gargle with fucoidan.

| $H_2O_2$ Gargle with fucoidan | Example 7 % (w/w) | Example 8 % (w/w) |
|---|---|---|
| Hydrogen Peroxide 3% | 50 | 50 |
| Fucoidan | 0.1 | 0.2 |
| HCl 10% | 0.0849 | 0.0849 |
| Sodium Benzoate | 0.05 | 0.05 |
| Menthol | 0.025 | 0.025 |
| Water | 49.74 | 49.64 |
| pH | 3.87 | 4.29 |
| Total osmolarity | 0.45 | 0.45 |

TABLE 6

Formulation of hydrogen peroxide gargle without fucoidan.

| $H_2O_2$ Gargle without fucoidan | Example 9 % (w/w) |
|---|---|
| Hydrogen Peroxide 3% | 50 |
| Sodium Benzoate | 0.05 |
| HCl 10% | 0.08495 |
| Menthol | 0.025 |
| Water | 49.84 |
| pH | 4.17 |
| Total osmolarity | 0.45 |

The antimicrobial properties of the composition of Examples 1, 2, and 7-9 are evaluated using ASTM E1052 test method. In an ASTM E1052 test, a suspension of virus is exposed to a test product at a ratio of 1:10 (1 part virus suspension+9 parts prepared test product). A Control suspension is concurrently processed in the same manner, with cell culture medium employed in place of the test product. Following neutralization, the suspensions are enumerated using standard cell culture (e.g. TCID50) or plaque assay techniques. Log 10 and percent reduction values are calculated to determine the effectiveness of the test product suspension relative to the control suspension.

According to this method MS2 Bacteriophage (MS2), ATCC 15597-B1 is the test virus. Bacterial cells are the hosts for bacteriophages, and E. coli 15597 serves this purpose for MS2 bacteriophage.

In summary the method includes the steps of:

Stock virus is thawed.

Test and control substances are dispensed in 9-part equivalent volumes into sterile vessels.

Test and control substances are each inoculated with 1-part equivalent volumes of the test virus.

The test suspensions are held for the contact time(s), and then neutralized by ten-fold serial dilutions into the appropriate solution. Gel filtration is employed.

The control suspension is neutralized in the same manner as the test suspensions.

Viral suspensions are quantified to determine the levels of growth

Infectious virus using standard cell culture (e.g. TCID50) or plaque assay techniques, samples are incubated for the period most suitable for the virus-host cell system (e.g. 7 days).

After the incubation period, the assay is scored for the presence/absence of test virus and cytotoxic effects. The appropriate calculations are performed (e.g. Spearman-Karber) to determine viral titers and levels of test substance cytotoxicity, where applicable.

Viral titers are computed for test suspensions relative to the control.

The test results are summarized in Table 7.

TABLE 7 bacteriophage inhibition of the Examples 1, 2, and 7-9.

| Test Microorganism | Contact Time | Test Substance | Replicate | PFU/ml | Average PFU/ml | Percent Reduction Compared to Control at Time Zero | $\text{Log}_{10}$ Reduction Compared to Control at Time Zero |
|---|---|---|---|---|---|---|---|
| MS2 ATCC 15597- | Time Zero | Control | 1 | 8.65E+05 | 1.20E+06 | N/A | |
| | | | 2 | 7.70E+05 | | | |
| | | | 3 | 1.95E+06 | | | |
| | 30 Seconds | Ex. 1 | 1 | 2.59E+05 | 2.09E+05 | 82.55% | 0.76 |
| | | | 2 | 1.86E+05 | | | |
| | | | 3 | 1.81E+05 | | | |
| | | Ex. 2 | 1 | 3.00E+05 | 2.51E+05 | 78.97% | 0.68 |
| | | | 2 | 2.22E+05 | | | |
| | | | 3 | 2.32E+05 | | | |
| | | Ex. 7 | 1 | 1.97E+05 | 1.90E+05 | 84.10% | 0.80 |
| | | | 2 | 2.18E+05 | | | |
| | | | 3 | 1.56E+05 | | | |
| | | Ex. 8 | 1 | 1.02E+05 | 9.55E+04 | 92.01% | 1.10 |
| | | | 2 | 8.80E+04 | | | |
| | | | 3 | 9.65E+04 | | | |
| | | Ex. 9 | 1 | 2.08E+05 | 2.07E+05 | 82.68% | 0.76 |
| | | | 2 | 2.06E+05 | | | |
| | | | 3 | 1.66E+05 | | | |

To further evaluate antimicrobial properties of the inventive compositions, Minimum Inhibitory Concentration Method (MIC) is performed. This is a general microbiological test method that is used to measure the lowest level of an antimicrobial agent that can inhibit microbial proliferation in liquid. The procedure is summarized as follows:

Test microorganisms are prepared in liquid culture medium for bacteria or on agar for fungi.

The test substance is prepared by conducting several serial 1:1 dilutions in a 96-well microtiter r in small test tubes, through Mueller-Hinton broth or other appropriate medium.

All wells or tubes containing diluted test substances are inoculated with test microorganisms, individually, resulting in one additional and final dilution of the product in all test vessels.

The microtiter plate or test tubes are incubated for 18-24 hours.

After the incubation period, observations are made.

The results for various organisms are detailed in Tables 8-13.

TABLE 8

24 hour results for Examples 1-3.

| Test Microorganism | Test Substance | 24 Hour Result |
|---|---|---|
| E. coli | Solution Ex. 3 | − |
| ATCC 8739 | Solution Ex. 1 | + |
| | Solution Ex. 2 | − |
| H. influenzae | Solution Ex. 3 | − |
| ATCC 8149 | Solution Ex. 1 | − |
| | Solution Ex. 2 | − |
| K. pneumoniae | Solution Ex. 3 | − |
| ATCC 29019 | Solution Ex. 1 | + |
| | Solution Ex. 2 | − |
| L. acidophilus | Solution Ex. 3 | + |
| ATCC 4356 | Solution Ex. 1 | + |
| | Solution Ex. 2 | + |
| M. catarrhalis | Solution Ex. 3 | − |
| ATCC 25238 | Solution Ex. 1 | − |
| | Solution Ex. 2 | − |
| P. aeruginosa | Solution Ex. 3 | + |
| ATCC 15442 | Solution Ex. 1 | + |
| | Solution Ex. 2 | − |
| P. mirabilis | Solution Ex. 3 | + |

TABLE 8-continued 24 hour results for Examples 1-3.

| Test Microorganism | Test Substance | 24 Hour Result |
|---|---|---|
| ATCC 7002 | Solution Ex. 1 | + |
| | Solution Ex. 2 | − |
| S. pneumoniae | Solution Ex. 3 | − |
| ATCC 49619 | Solution Ex. 1 | + |
| | Solution Ex. 2 | + |
| S. pyogenes | Solution Ex. 3 | + |
| ATCC 19615 | Solution Ex. 1 | + |
| | Solution Ex. 2 | + |
| S. aureus | Solution Ex. 3 | + |
| ATCC 33592 | Solution Ex. 1 | + |
| | Solution Ex. 2 | − |

TABLE 9

24 hour results for Examples 4-6.

| Test Microorganism | Test Substance | 24 Hour Result |
|---|---|---|
| L. acidophilus | Solution EX. 6 | + |
| ATCC 4356 | Solution Ex. 4 | + |
| | Solution Ex. 5 | + |
| S. sobrinus | Solution Ex. 6 | + |
| ATCC 33478 | Solution Ex. 4 | + |
| | Solution Ex. 5 | + |
| S. sobrinus | Solution EX. 6 | + |
| ATCC 33478 | Solution Ex. 4 | + |
| | Solution Ex. 5 | + |
| ATCC 25175 | Solution EX. 6 | − |
| | Solution Ex. 4 | − |
| | Solution Ex. 5 | − |

TABLE 10

24 hour results for Examples 7-9.

| Test Microorganism | Test Substance | 24 Hour Result |
|---|---|---|
| H. influenzae | Solution Ex. 9 | − |
| ATCC 8149 | Solution Ex. 7 | + |
| | Solution Ex. 8 | − |

TABLE 10-continued 24 hour results for Examples 7-9.

| Test Microorganism | Test Substance | 24 Hour Result |
|---|---|---|
| S. pneumoniae ATCC 49619 | Solution Ex. 9 | − |
|  | Solution Ex. 7 | − |
|  | Solution Ex. 8 | − |
| S. pyogenes | Solution Ex. 9 | − |
| ATCC 19615 | Solution Ex. 7 | − |
|  | Solution Ex. 8 | − |

TABLE 11

MIC and MBC results for Examples 1-3.

| Test Microorganism | CFU/ml Results | Test Substance | MIC | MBC | Positive Control | Negative Control |
|---|---|---|---|---|---|---|
| E. coli ATCC 8739 | 2.05E+05 | Solution EX. 3 | No Growth Observed | No MBC Observed | + | − |
|  |  | Solution Ex. 1 | Growth Observed | No MBC Observed | + | − |
|  |  | Solution Ex. 2 | No Growth Observed | No MBC Observed | + | − |
| H. influenzae ATCC 8149 | 3.15E+06 | Solution Ex. 3 | No Growth Observed | No MBC Observed | + | − |
|  |  | Solution Ex. 1 | No Growth Observed | No MBC Observed | + | − |
|  |  | Solution Ex. 2 | No Growth Observed | No MBC Observed | + | − |
| K. pneumoniae ATCC 29019 | 3.00E+04 | Solution Ex. 3 | No Growth Observed | No MBC Observed | + | − |
|  |  | Solution Ex. 1 | Growth Observed | No MBC Observed | + | − |
|  |  | Solution Ex. 2 | No Growth Observed | No MBC Observed | + | − |
| L. acidophilus ATCC 4356 | 3.15E+06 | Solution Ex. 3 | Growth Observed | No MBC Observed | + | − |
|  |  | Solution Ex. 1 | Growth Observed | No MBC Observed | + | − |
|  |  | Solution Ex. 2 | Growth Observed | No MBC Observed | + | − |
| M. catarrhalis ATCC 25238 | 4.35E+06 | Solution Ex. 3 | No Growth Observed | No MBC Observed | + | − |
|  |  | Solution Ex. 1 | No Growth Observed | No MBC Observed | + | − |
|  |  | Solution Ex. 2 | No Growth Observed | No MBC Observed | + | − |
| P. aeruginosa ATCC 15442 | 2.05E+04 | Solution Ex. 3 | Growth Observed | No MBC Observed | + | − |
|  |  | Solution Ex. 1 | Growth Observed | No MBC Observed | + | − |
|  |  | Solution Ex. 2 | No Growth Observed | No MBC Observed | + | − |
| P. mirabilis ATCC 7002 | 7.65E+05 | Solution Ex. 3 | Growth Observed | No MBC Observed | + | − |
|  |  | Solution Ex. 1 | Growth Observed | No MBC Observed | + | − |
|  |  | Solution Ex. 2 | No Growth Observed | No MBC Observed | + | − |
| S. pneumoniae ATCC 49619 | 1.75E+04 | Solution Ex. 3 | No Growth Observed | MBC Observed | + | − |
|  |  | Solution Ex. 1 | Growth Observed | No MBC Observed | + | − |
|  |  | Solution Ex. 2 | Growth Observed | No MBC Observed | + | − |
| S. pyogenes ATCC 19615 | 1.15E+06 | Solution Ex. 3 | Growth Observed | No MBC Observed | + | − |
|  |  | Solution Ex. 1 | Growth Observed | No MBC Observed | + | − |
|  |  | Solution Ex. 2 | Growth Observed | No MBC Observed | + | − |
| S. aureus ATCC 33592 | 2.40E+05 | Solution Ex. 3 | Growth Observed | No MBC Observed | + | − |
|  |  | Solution Ex. 1 | Growth Observed | No MBC Observed | + | − |
|  |  | Solution Ex. 2 | No Growth Observed | No MBC Observed | + | − |

TABLE 12

MIC and MBC results for Examples 4-6.

| Test Microorganism | CFU/ml Results | Test Substance | MIC | MBC | Positive Control | Negative Control |
|---|---|---|---|---|---|---|
| L. acidophils ATCC 4356 | 3.00E+05 | Solution Ex. 5 | Growth Observed | No MBC Observed | + | − |
| | | Solution Ex. 4 | Growth Observed | No MBC Observed | + | − |
| | | Solution Ex. 6 | Growth Observed | No MBC Observed | + | − |
| S. sobrinus ATCC 33478 | 5.40E+04 | Solution Ex. 4 | Growth Observed | No MBC Observed | + | − |
| | | Solution Ex. 5 | Growth Observed | No MBC Observed | + | − |
| S. mutans ATCC 25175 | 8.00E+05 | Solution Ex. 6 | Growth Observed | No MBC Observed | + | − |
| | | Solution Ex. 4 | No Growth Observed | MBC Observed | + | − |
| | | Solution Ex. 5 | No Growth Observed | MBC Observed | + | − |

TABLE 13

MIC and MBC results for Examples 7-9.

| Test Microorganism | CFU/ml Results | Test Substance | MIC | MBC | Positive Control | Negative Control |
|---|---|---|---|---|---|---|
| S. influenenzae ATCC 8149 | 3.15E+06 | Solution Ex. 9 | No Growth Observed | No MBC Observed | + | − |
| | | Solution Ex. 7 | No Growth Observed | No MBC Observed | + | − |
| | | Solution Ex. 8 | No Growth Observed | MBC Observed | + | − |
| S. pneumoniae ATCC 49619 | 1.75E+04 | Solution Ex. 9 | No Growth Observed | MBC | + | − |
| | | Solution Ex. 7 | No Growth Observed | MBC | + | − |
| | | Solution Ex. 8 | No Growth Observed | MBC | + | − |
| S. pyogenes ATCC 19615 | 1.15E+06 | Solution Ex. 9 | No Growth Observed | MBC | + | − |
| | | Solution Ex. 7 | No Growth Observed | MBC | + | − |
| | | Solution Ex. 9 | No Growth Observed | MBC | + | − |

Any patents or publications mentioned in this specification are herein incorporated by reference to the same extent as if each individual publication was specifically and individually indicated to be incorporated by reference.

The foregoing description is illustrative of particular embodiments of the invention, but is not meant to be a limitation upon the practice thereof.

The invention claimed is:

1. A storage stable package comprising:
a polymeric bottle having a volume;
an aqueous saline composition acidified with mineral acid to a pH of 3.0 to 7.0 and having a hypertonic saline concentration relative to saliva and blood to achieve a storage stability at 20 degrees Celsius of the composition of at least 10 weeks, said aqueous composition independent of a synthetic antimicrobial and free of phenols and ethanol; and
a cap for selectively sealing said aqueous saline composition within the volume.

2. The package of claim 1 wherein said acid is hydrochloric acid.

3. The package of claim 1 wherein said acid is hydrobromic, phosphoric, sulfuric, nitric, or a combination thereof.

4. The package of claim 1 wherein said pH is 3.6 to 5.4.

5. The package of claim 1 further comprising a flavorant.

6. The package of claim 1 further comprising a desensitizer.

7. The package of claim 1 further comprising a fluoridation agent.

8. The package of claim 1 further comprising fucoidan.

9. The package of claim 8 wherein said fucoidan is present from 0.1 to 2.0 total weight percent of the said aqueous saline composition.

10. The package of claim 1 wherein the hypertonic saline concentration is between 1.7 and 5.0 total weight percent of the said aqueous saline composition.

11. A storage stable package comprising:
a polymeric bottle having a volume;
an aqueous hydrogen peroxide composition acidified with mineral acid to a pH of 2.7 to 5.3 and having a hydrogen peroxide concentration 0.5 to 2.5 total weight percent of said aqueous hydrogen peroxide composition to achieve a storage stability at 20 degrees Celsius of the composition of at least 10 weeks, said aqueous composition independent of a small molecule organic synthetic antimicrobial and free of phenols and ethanol; and a cap for selectively sealing said aqueous saline composition within the volume.

12. The package of claim 11 wherein said acid is hydrochloric acid.

13. The package of claim 11 wherein said acid is hydrobromic, phosphoric, sulfuric, nitric, or a combination thereof.

14. The package of claim 11 wherein said pH is 3.0 to 5.0.

15. The package of claim 11 wherein said pH is 3.6 to 4.4.

16. The package of claim 11 further comprising a desensitizer.

17. The package of claim 11 further comprising a fluoridation agent.

18. The package of claim 11 further comprising fucoidan.

19. The package of claim 18 wherein said fucoidan is present from 0.1 to 2.0 total weight percent of the said aqueous hydrogen peroxide composition.

20. A process for treating an infection of a pharyngeal or buccal cavity comprising: rinsing the pharyngeal or buccal cavity with said aqueous saline composition of claim 1 for an amount of time sufficient to treat the infection; and expectorating said aqueous saline composition.

21. The process of claim 20 wherein rinsing is gargling.

22. A process for treating an infection of a pharyngeal or buccal cavity comprising: rinsing the pharyngeal or buccal cavity with said hydrogen peroxide composition of claim 11 for an amount of time sufficient to treat the infection; and expectorating said hydrogen peroxide composition.

23. The process of claim 22 wherein rinsing is gargling.

* * * * *